United States Patent [19]

Tsien et al.

[11] Patent Number: 5,625,048
[45] Date of Patent: Apr. 29, 1997

[54] MODIFIED GREEN FLUORESCENT PROTEINS

[75] Inventors: Roger Y. Tsien, La Jolla; Roger Heim, Del Mar, both of Calif.

[73] Assignee: The Regents of the University of California

[21] Appl. No.: 337,915

[22] Filed: Nov. 10, 1994

[51] Int. Cl.$^6$ .................................................. C07H 21/04
[52] U.S. Cl. ........................... 536/23.4; 435/6; 536/23.5
[58] Field of Search ............................... 435/6; 536/23.5, 536/23.4

[56] References Cited

PUBLICATIONS

Ehrig et al. (1995) *FEBS Letters* 367 (2):163–166. Green-fluorescent protein mutants with altered fluorescence excitation spectra.
Heim et al. (1994) *PNAS* 91 (26):12501–12505. Wavelength mutations and posttranslational autoxidation of green fluorescent protein.
Delagrave et al. (1995) *Bio/Technology* 13:151–154. Red-Shifted Excitation Mutants of the Green Fluorescent Protein.
Kain et al. (1995) *BioTechniques* 19 (4):650–655. Green Fluorescent Protein as a Reporter of Gene Expression and Protein Localization.
Heim et al. (1995) *Nature* 373:663–664. Improved green fluorescence.
Cody, C. W. et al., *Biochemistry* 32, 1212–1218 (1993).
Prasher, D. C. et al., *Gene* 111, 229–233 (1992).
Chalfie, M. et al., *Science* 263, 802–805 (1994).
Ward, W. W. & Bokman, S. H., *Biochemistry* 21, 4535–4540 (1982).
Surpin, M. A. & Ward, W. W., *Photochem. Photobiol.* 49, Abstract, 25S (1989).
Muhlrad, D. et al., *Yeast* 8, 79–82 (1992).

*Primary Examiner*—Jasemine C. Chambers
*Assistant Examiner*—Scott D. Priebe
*Attorney, Agent, or Firm*—Townsend and Townsend and Crew, L.L.P.

[57] ABSTRACT

Modifications in the sequence of Aequorea wild-type GFP provide products having markedly different excitation and emission spectra from corresponding products from wild-type GFP. In one class of modifications, the product derived from the modified GFP exhibits an alteration in the ratio of two main excitation peaks observed with the product derived from wild-type GFP. In another class, the product derived from the modified GFP fluoresces at a shorter wavelength than the corresponding product from wild-type GFP. In yet another class of modifications, the product derived from the modified GFP exhibits only a single excitation peak and enhanced emission relative to the product derived from wild-type GFP.

25 Claims, 6 Drawing Sheets

MODIFIED GREEN FLUORESCENT PROTEINS

This invention was made with Government support under Grant No. NS27177, awarded by the National Institute of Health. The Government has certain rights in this invention.

BACKGROUND OF THE INVENTION

This invention relates generally to the fields of biology and chemistry. More particularly, the invention is directed to modified fluorescent proteins and to methods for the preparation and use thereof.

In biochemistry, molecular biology and medical diagnostics, it is often desirable to add a fluorescent label to a protein so that the protein can be easily tracked and quantified. The normal procedures for labeling requires that the protein be covalently reacted in vitro with fluorescent dyes, then repurified to remove excess dye and any damaged protein. If the labeled protein is to be used inside cells, it usually has to be microinjected; this is a difficult and time-consuming operation that cannot be performed on large numbers of cells. These problems may, however, be eliminated by joining a nucleotide sequence coding for the protein of interest with the sequence for a naturally fluorescent protein, then expressing the fusion protein.

The green fluorescent protein (GFP) of the jellyfish *Aequorea victoria* is a remarkable protein with strong visible absorbance and fluorescence from a p-hydroxybenzylideneimidazolone chromophore, which is generated by cyclization and oxidation of the protein's own Ser-Tyr-Gly sequence at positions 65 to 67. A cDNA sequence [SEQ ID NO:1] for one isotype of GFP has been reported [Prasher, D.C. et al., *Gene* 111, 229–233 (1992)]; cloning of this cDNA has enabled GFP expression in different organisms. The finding that the expressed protein becomes fluorescent in cells from a wide variety of organisms [Chalfie, M. et al., *Science* 263, 802–805 (1994)] makes GFP a powerful new tool in molecular and cell biology and indicates that the oxidative cyclization must be either spontaneous or dependent only on ubiquitous enzymes and reactants.

A major question in protein photophysics is how a single chromophore can give widely different spectra depending on its local protein environment. This question has received the most attention with respect to the multiple colors of visual pigments based on retinal [Merbs, S. L. & Nathans, J. *Science* 258, 464–466 (1992)], but is also important in GFP. The GFP from Aequorea and that of the sea pansy *Renilla reniformis* share the same chromophore, yet Aequorea GFP has two absorbance peaks at 395 and 475 nm, whereas Renilla GFP has only a single absorbance peak at 498 nm, with about 5.5 fold greater monomer extinction coefficient than the major 395 nm peak of the Aequorea protein [Ward, W. W. in *Biohtminescence and Chemiluminescence* (eds. DeLuca, M. A. & McElroy, W. D.) 235–242 (Academic Press, New York, 1981)]. The spectra of the isolated chromophore and denatured protein at neutral pH do not match the spectra of either native protein [Cody, C. W. et al., *Biochemistry* 32, 1212–1218 (1993)].

For many practical applications, the spectrum of Renilla GFP would be preferable to that of Aequorea, because wavelength discrimination between different fluorophores and detection of resonance energy transfer are easier if the component spectra are tall and narrow rather than low and broad. Furthermore, the longer wavelength excitation peak (475 nm) of Aequorea GFP is almost ideal for fluorescein filter sets and is resistant to photobleaching, but has lower amplitude than the shorter wavelength peak at 395 nm, which is more susceptible to photobleaching [Chalfie et al. (1994), supra]. For all these reasons, it would clearly be advantageous to convert the Aequorea GFP excitation spectrum to a single peak, and preferably at longer wavelengths.

Accordingly, it is an object of the present invention to provide improved fluorescent proteins which do not suffer from the drawbacks of native Aequorea GFP.

SUMMARY OF THE INVENTION

In accordance with the present invention, it has been determined that particular modifications in the polypeptide sequence of an Aequorea wild-type GFP [SEQ ID NO:2] lead to formation of products having markedly different excitation and emission spectra from corresponding products derived from wild-type GFP. Visibly distinct colors and/or increased intensities of emission make these products useful in a wide variety of contexts, such as tracking of differential gene expression and protein localization.

BRIEF DESCRIPTION OF THE DRAWINGS

The invention may be better understood with reference to the accompanying drawings, in which.

DETAILED DESCRIPTION OF THE INVENTION

GFP was expressed in *E. coli* under the control of a T7 promoter for quantitative analysis of the properties of the recombinant protein. Gel electrophoresis under denaturing conditions showed protein of the expected molecular weight (27 kDa) as a dominant band (FIG. 1), which could be quantified simply by densitometry of staining with Coomassie blue. Soluble recombinant GFP proved to have identical spectra and the same or even slightly more fluorescence per mole of protein as GFP purified from *Aequorea victoria*, showing that the soluble protein in *E. coli* undergoes correct folding and oxidative cyclization with as high an efficiency as in the jellyfish.

Figure 1:
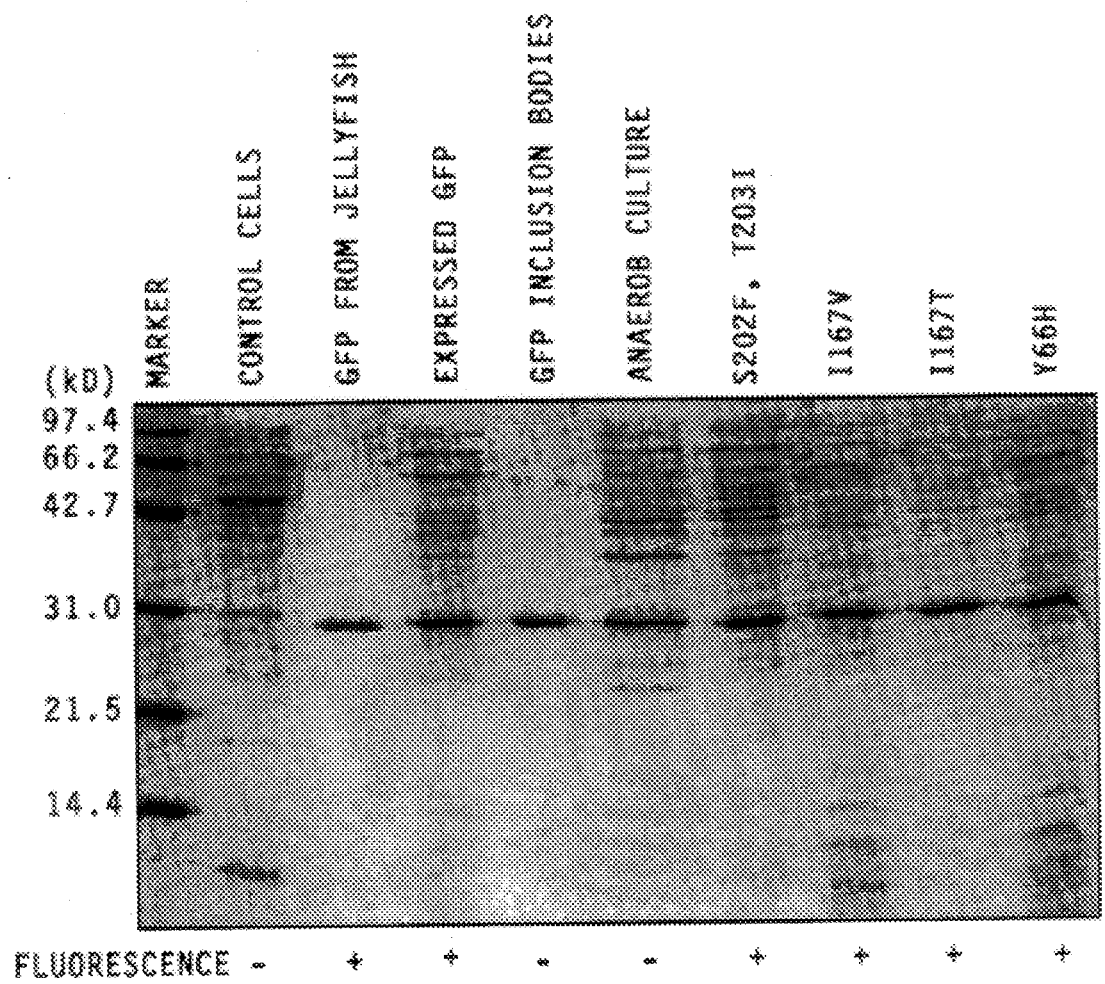
FIG. 1 compares different versions of GFP by gel electrophoresis and Coomassie blue staining.

The bacteria also contained inclusion bodies consisting of protein indistinguishable from jellyfish or soluble recombinant protein on denaturing gels (FIG. 1). However, this material was completely non-fluorescent, lacked the visible absorbance bands of the chromophore, and could not be made fluorescent even when solubilized and subjected to protocols that renature GFP [Ward, W. W. & Bokman, S. H., *Biochemistry* 21, 4535–4540 (1982); Surpin, M. A. & Ward, W. W., *Photochem. Photobiol.* 49, Abstract, 25S (1989)]. Therefore, protein from inclusion bodies seemed permanently unable to generate the internal chromophore. An interesting intermediate stage in protein maturation could be generated by growing the bacteria anaerobically. The soluble protein again looked the same as GFP on denaturing gels (FIG. 1) but was non-fluorescent. In this case, fluorescence gradually developed after admission of air, even when fresh protein synthesis was blocked using puromycin and tetracycline. Evidently, the soluble non-fluorescent protein synthesized under anaerobic conditions was ready to become fluorescent once atmospheric oxygen was reemitted. The fluorescence per protein molecule approached its final asymptotic value with a single-exponential time course and a rate constant of 0.24±0.06 hr$^{-1}$ (at 22° C.) measured either in intact cells with protein-synthesis inhibitors or in a lysate in which the soluble proteins and cofactors were a thousand fold more dilute. Such pseudo-first order kinetics strongly suggest that no enzymes or cofactors are necessary for the final step of fluorophore formation in GFP.

It has thus been determined that formation of the final fluorophore requires molecular oxygen and proceeds in wild-type protein with a time constant of ~4 h at 22° C. and atmospheric $pO_2$. This was independent of dilution, implying that the oxidation does not require enzymes or cofactors.

Figure 2:
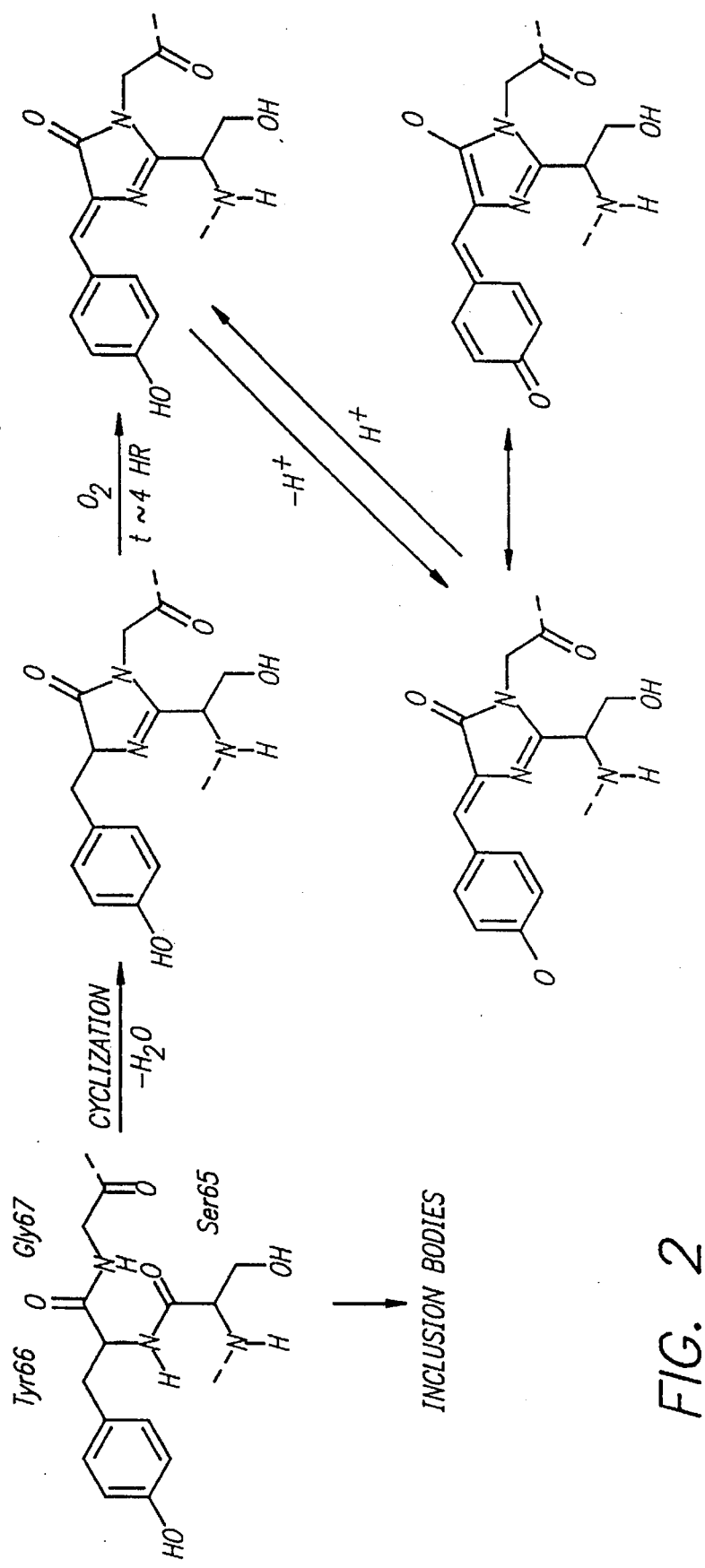
FIG. 2 illustrates a proposed biosynthetic scheme for GFP.

A molecular interpretation is presented in FIG. 2. If the newly translated apoprotein (top left) evades precipitation into inclusion bodies, the amino group of Gly 67 might cyclize onto the carbonyl group of Ser 65 to form an imidazolidin-5-one, where the process would stop (top center) if $O_2$ is absent. The new N=C double bond would be expected to promote dehydrogenation to form a conjugated chromophore; imidazolidin-5-ones are indeed known to undergo autoxidative formation of double bonds at the 4-position [Kjaer, A. *Acta Chem. Scand.* 7, 1030–1035 (1953); Kidwai, A. R. & Devasia, G. M. *J. Org. Chem.* 27, 4527–4531 (1962)], which is exactly what is necessary to complete the fluorophore (upper right). The protonated and deprotonated species (upper right and lower right) may be responsible for the 395 and 470–475 nm excitation peaks, respectively. The excited states of phenols are much more acidic than their ground states, so that emission would come only from a deprotonated species.

The Aequorea GFP cDNA was subjected to random mutagenesis by hydroxylamine treatment or polymerase chain reaction. Approximately six thousand bacterial colonies on agar plates were illuminated with alternating 395 and 475 nm excitation and visually screened for altered excitation properties or emission colors.

According to a first aspect of the present invention, modifications are provided which result in a shift in the ratio of the two excitations peaks of the product after oxidation and cyclization relative to the wild type. Three mutants were found with significant alterations in the ratio of the two main excitation peaks (Table I). The mutations were sequenced and recombined with the wild-type gene in different ways to eliminate neutral mutations and assign the fluorescence effects to single amino acid substitutions, except for H9 where two neighboring mutations have not yet been separated. They all lay in the C terminal part of the protein (Table I), remote in primary sequence from the chromophore formed from residues 65–67.

These and other modifications are defined herein with reference to the amino acid sequence [SEQ ID NO:2] encoded by the reported cDNA [SEQ ID NO:1]; the first amino acid identified is the one found at the indicated location in the reported sequence, while the second indicates the substitution found in the modified form. The fluorescent product derived from a wild-type or modified GFP polypeptide sequence is no longer strictly speaking a simple polypeptide after oxidation and cyclization; however, reference is sometimes made for sake of simplicity herein to the polypeptide (e.g., "wild-type GFP" or "modified GFP") where what is intended would be obvious from the context. Compared with wild-type GFP, H9 (Ser 202→Phe, Thr 203→Ile) had increased fluorescence at 395 nm excitation; P9 (Ile 167→Val) and P11 (Ile 167→Thr) were more fluorescent at 475 nm excitation.

One possibility for these spectral perturbations in P9 and P11 is that the mutations at Ile 167 shift a positive charge slightly closer to the phenolic group of the fluorophore; this should both increase the percentage of phenolic anion, which is probably the species responsible for the 470–475 nm excitation peak, and shift the emission peak hypsochromically. However, the hypothesized ionizable phenolic group would have to be buried inside the protein at normal pH, because the ratio of 471 to 396 nm peaks in the mutants could not be further affected by external pH until it was raised to 10, just below the threshold for denaturation. The pH-sensitivity of wild-type GFP is similar [Ward, W. W. et al., *Photochem. Photobiol.* 35, 803–808 (1982)].

According to another aspect of the invention, a fourth mutant P4 (Tyr 66→His) was identified which was excitable by ultraviolet and fluoresced bright blue in contrast to the green of wild type protein. The excitation and emission maxima were hypsochromically shifted by 14 and 60 nm respectively from those of wild-type GFP. The mutated DNA was sequenced and found to contain five amino acid substitutions, only one of which proved to be critical: replacement of Tyr 66 in the center of the chromophore by His (corresponding to a change in the GFP cDNA sequence [SEQ ID NO:1] at 196–198 from TAT to CAT).

The surprising tolerance for substitution at this key residue prompted further site-directed mutagenesis to Trp and Phe at this position. Trp gave excitation and emission wavelengths intermediate between Tyr and His (Table 1) but was only weakly fluorescent, perhaps due to inefficiency of folding or chromophore formation due to steric considerations. Phe gave no detectable fluorescence. Accordingly, pursuant to this aspect of the invention modified GFP proteins which fluoresce at different wavelengths (preferably, different by at least 10 nm and more preferably, by at least 50 nm) relative to the native protein are provided, for example, those wherein Tyr 66 is replaced by His or Trp.

Pursuant to yet another aspect of the present invention, modified GFP proteins are provided which provide substantially more intense fluorescence per molecule than the wild type protein. Modifications at Ser 65 to Ala, Leu, Cys, Val, Ile or Thr provide proteins with red-shifted and brighter spectra relative to the native protein. In particular, the Thr mutant (corresponding to a change in the GFP cDNA sequence [SEQ ID NO:1] at 193–195 from TCT to ACT) and Cys mutant (corresponding to a change in the GFP cDNA sequence [SEQ ID NO:1] at 193–195 from TCT to TGT) are about six times brighter than wild type when excited at the preferred long-wavelength band above 450 nm. As a consequence, these modified proteins are superior to wild type proteins for practically all applications. Further, the brightness of these modified proteins matches the brightness reported in the literature for Renilla GFP; thus, these proteins clearly obviate the objections to the dimness of Aequorea GFP. In fact, it is speculated that the chromophores in these modified proteins may exhibit the optimum brightness which could be achieved with a general structure derived from the Aequorea GFP chromophore. In particular, these mutations provide products exhibiting one or more of the following salient characteristics which distinguish them clearly over the corresponding product from a wild-type GFP: reduced efficiency of excitation by wavelengths between about 350 and 420 nm; enhanced excitation and emission efficiency when excited with wavelengths longer than about 450 nm; increased resistance to light-induced shifts in the excitation spectrum; and faster kinetics of fluorophore generation. In contrast, mutations to Trp, Arg, Asn, Phe and Asp did not provide improved brightness.

As would be readily apparent to those working in the field, to provide the desired fluorescent protein it would not be necessary to include the entire sequence of GFP. In particular, minor deletions at either end of the protein sequence are expected to have little or no impact on the fluorescence spectrum of the protein. Therefore, by a mutant or wild-type GFP sequence for purposes of the present invention are contemplated not only the complete polypeptide and oligonucleotide sequences discussed herein, but also functionally-equivalent portions thereof (i.e., portions of the polypeptide sequences which exhibit the desired fluorescence properties and oligonucleotide sequences encoding these polypeptide sequences). For example, whereas the chromophore itself (position 65–67) is obviously crucial, the locations of known neutral mutations suggest that amino acids 76–115 are less critical to the spectroscopic properties of the product. In addition, as would be immediately apparent to those working in the field, the use of various types of fusion sequences which lengthen the resultant protein and serve some functional purpose in the preparation or purification of the protein would also be routine and are contemplated as within the scope of the present invention. For example, it is common practice to add amino acid sequences including a polyhistidine tag to facilitate purification of the product proteins. As such fusions do not significantly alter the salient properties of the molecules comprising same, modified GFPs as described herein including such fusion sequences at either end thereof are also clearly contemplated as within the scope of the present invention.

Similarly, in addition to the specific mutations disclosed herein, it is well understood by those working in the field that in many instances modifications in particular locations in the polypeptide sequence may have no effect upon the properties of the resultant polypeptide. Unlike the specific mutations described in detail herein, other mutations provide polypeptides which have properties essentially or substantially indistinguishable from those of the specific polypeptides disclosed herein. For example, the following substitutions have been found to be neutral (i.e., have no significant impact on the properties of the product): Lys 3→Arg; Asp 76→Gly; Phe 99→Ile; Asn 105→Ser; Glu 115→Val; Thr 225→Ser; and Lys 238→Glu. These equivalent polypeptides (and oligonucleotide sequences encoding these polypeptides) are also regarded as within the scope of the present invention. In general, the polypeptides and oligonucleotide sequences of the present invention (in addition to containing at least one of the specific mutations identified herein) will be at least about 85% homologous, more preferably at least about 90% homologous, and most preferably at least about 95% homologous, to the wild-type GFP described herein. Because of the significant difference in properties observed upon introduction of the specified modifications into a GFP sequence, the presence of the specified modifications relative to the corresponding reported sequence for wild-type GFP [SEQ ID NO:2] are regarded as central to the invention.

The oligonucleotide sequences of the present invention are particularly useful in processes for labelling polypeptides of interest, e.g., by the construction of genes encoding fluorescent fusion proteins. Fluorescence labeling via gene fusion is site-specific and eliminates the present need to purify and label proteins in vitro and microinject them into cells. Sequences encoding the modified GFPs of the present invention may be used for a wide variety of purposes as are well known to those working in the field. For example, the sequences may be employed as reporter genes for monitoring the expression of the sequence fused thereto; unlike other reporter genes, the sequences require neither substrates nor cell disruption to evaluate whether expression has be achieved. Similarly, the sequences of the present invention may be used as a means to trace lineage of a gene fused thereto during the development of a cell or organism. Further, the sequences of the present invention may be used as a genetic marker; cells or organisms labeled in this manner can be selected by, e.g., fluorescence-activated cell sorting. The sequences of the present invention may also be used as a fluorescent tag to monitor protein expression in vivo, or to encode donors or acceptors for fluorescence resonance energy transfer. Other uses for the sequences of the present invention would be readily apparent to those working in the field, as would appropriate techniques for fusing a gene of interest to an oligonucleotide sequence of the present invention in the proper reading frame and in a suitable expression vector so as to achieve expression of the combined sequence.

The availability of several forms of GFP with such different spectral properties should facilitate two-color assessment of differential gene expression, developmental fate, or protein trafficking. For example, if one wanted to screen for a drug that is specific to activate expression of gene A but not gene B, one could fuse the cDNA for one color of GFP to the promoter region of gene A and fuse the cDNA for another color to the promoter region of gene B. Both constructs would be transfected into target cells and the candidate drugs could be assayed to determine if they stimulate fluorescence of the desired color, but not fluorescence of the undesired color. Similarly, one could test for the simultaneous expression of both A and B by searching for the presence of both colors simultaneously.

As another example, to examine the precise temporal or spatial relationship between the generation or location of recombinant proteins X and Y within a cell or an organism, one could fuse genes for different colors of GFP to the genes for proteins X and Y, respectively. If desired, DNA sequences encoding flexible oligopeptide spacers could be included to allow the linked domains to function autonomously in a single construct. By examining the appearance of the two distinguishable colors of fluorescence in the very same cells or organisms, one could compare and contrast the generation or location of the proteins X and Y with much greater precision and less biological variability than if one had to compare two separate sets of cells or organisms, each containing just one color of GFP fused to either protein X or Y. Other examples of the usefulness of two colors would be obvious to those skilled in the art.

The invention may be better understood with reference to the accompanying examples, which are intended for purposes of illustration only and should not be construed as in any sense limiting the scope of the invention as defined by the claims appended hereto.

EXAMPLE 1

The coding region of GFP clone 10.1 [Prasher et al. (1992), supra] was amplified by PCR to create NdeI and BamHI sites at the 5' and 3' ends, respectively, and was cloned behind the T7 promoter of pGEMEX2 (Promega) replacing most of the T7 gene 10. The resulting plasmid was transformed into the strain JM109(DE3) (Promega Corp., Madison, Wis.), and high level expression was achieved by growing the cultures at 24° C. to saturation without induction by IPTG. To prepare soluble extracts, 1.5 ml cell suspension were collected, washed and resuspended in 150 µl 50 mM Tris/HCl, pH 8.0, 2 mM EDTA. Lysozyme and DNAse I were added to 0.2 mg/ml and 20 µg/ml, respectively, and the samples were incubated on ice until lysis occurred (1-2 hours). The lysates were then clarified by centrifuging at 12,000×g for 15 minutes. Inclusion bodies were obtained as described in the literature [Sambrook, J. et al. in *Molecular Cloning: A Laboratory Manual* Vol. 2, 17.37–17.41 (Cold Spring Harbor Press, Cold Spring Harbor, N.Y., 1989)].

As illustrated in FIG. 1, soluble extracts of *E. coli* expressing GFP show a predominant band which is absent in extracts from control cells and has the same electrophoretic mobility as native GFP isolated from the jellyfish *A. victoria*. Inclusion bodies of expressing cells consist mainly of non-fluorescent GFP which has the same mobility as soluble GFP. Non-fluorescent soluble GFP of anaerobically grown cultures is also a major band with correct mobility. Soluble extracts of the mutated clones H9, P9, P11 and P4 again contain a dominant protein with essentially the same molecular weight.

Random mutagenesis of the GFP cDNA was done by increasing the error rate of the polymerase chain reaction with 0.1 mM $MnCl_2$, 50 µM dATP and 200 µM of dGTP, dCTP, and dTTP [Muhlrad, D. et al., *Yeast* 8, 79–82 (1992)]. The product was ligated into pGEMEX2 and subsequently transformed into JM109(DE3). Colonies on agar were visually screened for different emission colors and ratios of brightness when excited at 475 vs. 395 nm.

Figure 3A:
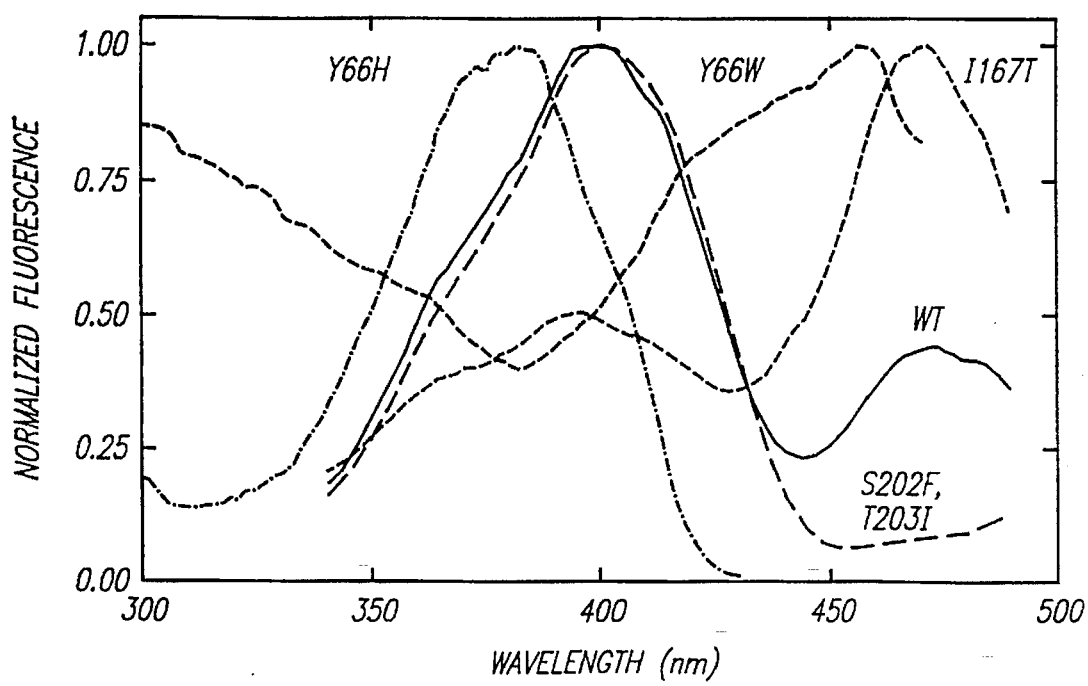
FIGS. 3a and 3b illustrate the excitation and emission spectra of wild-type and a first group of mutant GFPs.
Figure 3B:
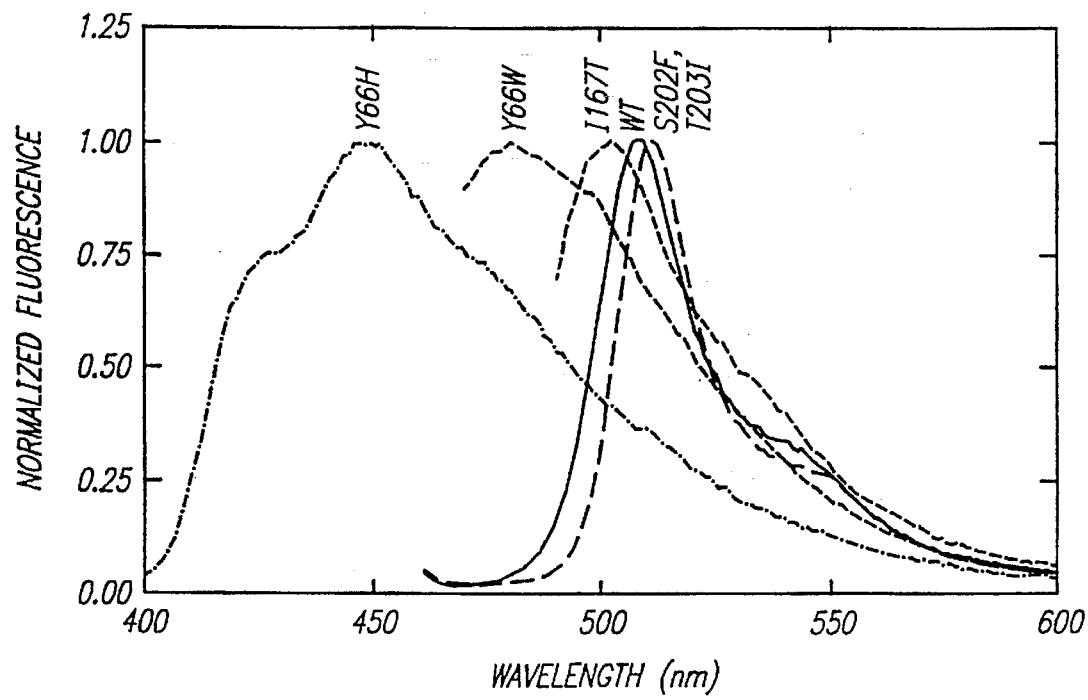

FIGS. 3a and 3b illustrate the excitation and emission spectra of wild-type and mutant GFPs. In FIGS. 3a and 3b, ——— wild-type; —— S202F.T203I; – – – 167T; ----- Y66W; — •— • Y66H. Samples were soluble fractions from *E. coli* expressing the proteins at high level, except for Y66W, which was obtained in very low yield and measured on intact cells. Autofluorescence was negligible for all spectra except those of Y66W, whose excitation spectrum below 380 nm may be contaminated by autofluorescence. Excitation and emission spectra were measured with 1.8 nm bandwidths and the non-scanning wavelength set to the appropriate peak. Excitation spectra were corrected with a rhodamine B quantum counter, while emission spectra (except for Y66W) were corrected for monochromator and detector efficiencies using manufacturer-supplied correction spectra. All amplitudes have been arbitrarily normalized to a maximum value of 1.0. A comparison of brightness at equal protein concentrations is provided in Table I.

TABLE I

Characteristics of mutated vs. wild-type GFP

| Variant | Mutation | Excitation Maxima (nm)[a] | Emission Maxima (nm)[b] | Relative[c] Fluorescence |
|---|---|---|---|---|
| Wild type | none | 396 (476) | 508 (503) | (≡100%) |
| H9 | Ser 202→Phe, Thr 203→Ile | 398 | 511 | 117%[d] |
| P9 | Ile 167→Val | 471 (396) | 502 (507) | 166%[e] |
| P11 | Ile 167→Thr | 471 (396) | 502 (507) | 188%[e] |
| P4 | Tyr 66→His | 382 | 448 | 57%[f] |
| W | Tyr 66→Trp | 458 | 480 | n.d. |

[a]Values in parentheses are lower-amplitude peaks.
[b]Primary values were observed when exciting at the main excitation peak; values in parentheses were observed when illuminating at the lower-amplitude excitation peak.
[c]Equal amounts of protein were used based on densitometry of gels stained with Coomassie Blue (FIG. 1).
[d]Emission maxima of spectra recorded at excitation 395 nm were compared.
[e]Emission maxima of spectra recorded at excitation 475 nm were compared.
[f]Emission spectrum of P4 recorded at 378 nm excitation was integrated and compared to the integrated emission spectrum of wild type recorded at 475 nm excitation; both excitation and emission characteristics were corrected.

EXAMPLE 2

Oligonucleotide-directed mutagenesis at the codon for Ser-65 of GFP cDNA was performed by the literature method [Kunkel, T. A. (1985) *Proc. Natl. Acad. Sci. USA* 82, 488] using the Muta-Gene Phagemid in Vitro Mutagenesis Kit version 2, commercially available from Bio-Rad, Richmond, Calif. The method employs a bacterial host strain deficient for dUTPase (dut) and uracil-N-glycosylase (ung), which results in an occasional substitution of uracil for thymine in newly-synthesized DNA. When the uracil-containing DNA is used as a wild-type template for oligonucleotide-directed in vitro mutagenesis, the complementary (mutant) strand can be synthesized in the presence of deoxynucleotides, ligase and polymerase using the mutagenic oligonucleotide to prime DNA synthesis; the Version 2 kit utilizes unmodified T7 DNA polymerase to synthesize the complementary strand. When the heteroduplex molecule is transformed into a host with an active uracil-N-glycosylase (which cleaves the bond between the uracil base and the ribose molecule, yielding an apyrimidic site), the uracil-containing wild-type strand is inactivated, resulting in an enrichment of the mutant strand.

The coding region of GFP cDNA was cloned into the BamHI site of the phagemid $pRSET_B$ from Invitrogen (San Diego, Calif.). This construct was introduced into the *dut, ung* double mutant *E. coli* strain CJ236 provided with the Muta-Gene kit and superinfected with helper phage VCSM13 (Stratagene, La Jolla, Calif.) to produce phagemid particles with single-stranded DNA containing some uracils in place of thymine. The uracil-containing DNA was purified to serve as templates for in vitro synthesis of the second strands using the mutagenic nucleotides as primers. The DNA hybrids were transformed into the strain XL1blue (available from Stratagene), which has a functional uracil-N-glycosylase; this enzyme inactivates the parent wild-type DNA strand and selects for mutant clones. DNA of several colonies were isolated and checked for proper mutation by sequencing.

To express the mutant proteins, the DNA constructs obtained by mutagenesis were transformed into E. coli strain BL21(DE3)LysS (Novagen, Madison, Wis.), which has a chromosomal copy of T7 polymerase to drive expression from the strong T7 promotor. At room temperature 3 ml cultures were grown to saturation (typically, overnight) without induction. Cells from 1 ml of culture were collected, washed and finally resuspended in 100 µl of 50 mM Tris pH 8.0, 300 mM NaCl. The cells were then lysed by three cycles of freeze/thawing (liquid nitrogen/30° C. water bath). The soluble fraction was obtained by pelletting cell debris and unbroken cells in a microfuge.

To facilitate purification of the recombinant proteins, the vector used fuses a histidine tag (6 consecutive His) to the N-terminus of the expressed proteins. The strong interaction between histidine hexamers and $Ni^{2+}$ ions permitted purification of the proteins by NI-NTA resin (available commercially from Qiagen, Chatsworth, Calif.). Microcolumns (10 µl bed volume) were loaded with 100 µl soluble extract (in 50 mM Tris pH 8.0, 300 mM NaCl), washed with 10 bed volumes of the same buffer and with 10 volumes of the buffer containing 20 mM imidazole. The recombinant proteins were then eluted with the same buffer containing 100 mM imidazole.

Aliquots of the purified mutant GFP proteins were run along with wild-type GFP on a denaturing polyacrylamide gel. The gel was stained with Coomassie blue and the protein bands were quantified by scanning on a densitometer. Based on these results, equal amounts of each version of protein were used to run fluorescence emission and excitation spectra.

Figure 4A:
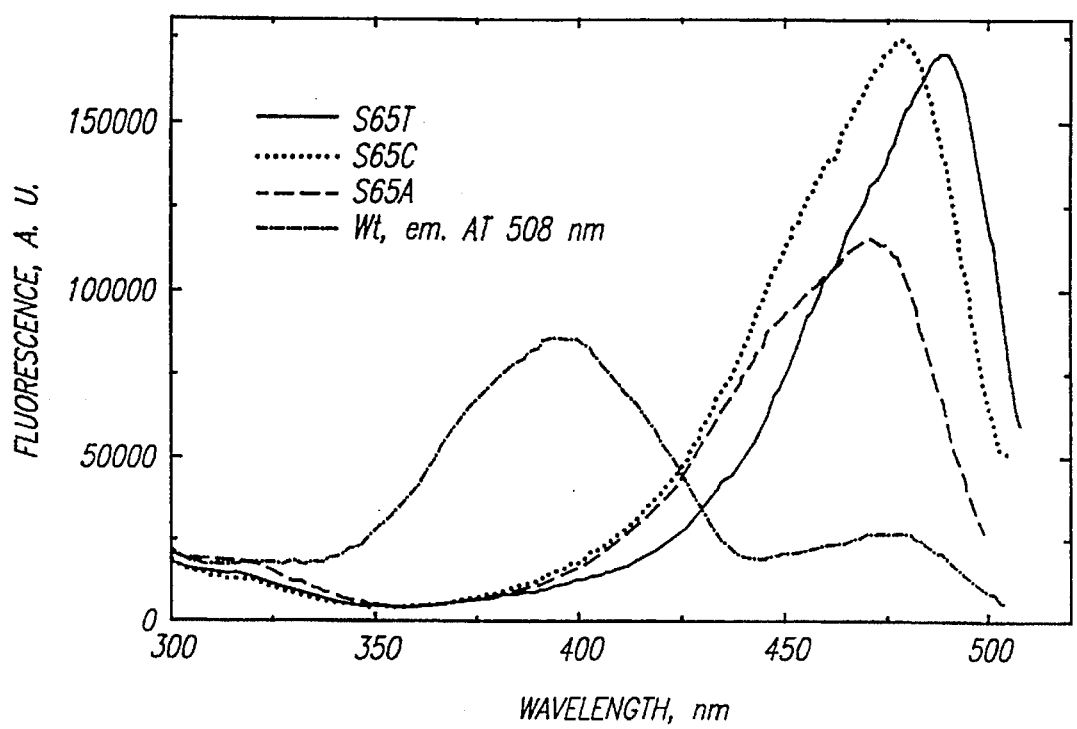
FIGS. 4a and 4b illustrate the excitation and emission spectra of wild-type and a second group of mutant GFPs.
Figure 4B:
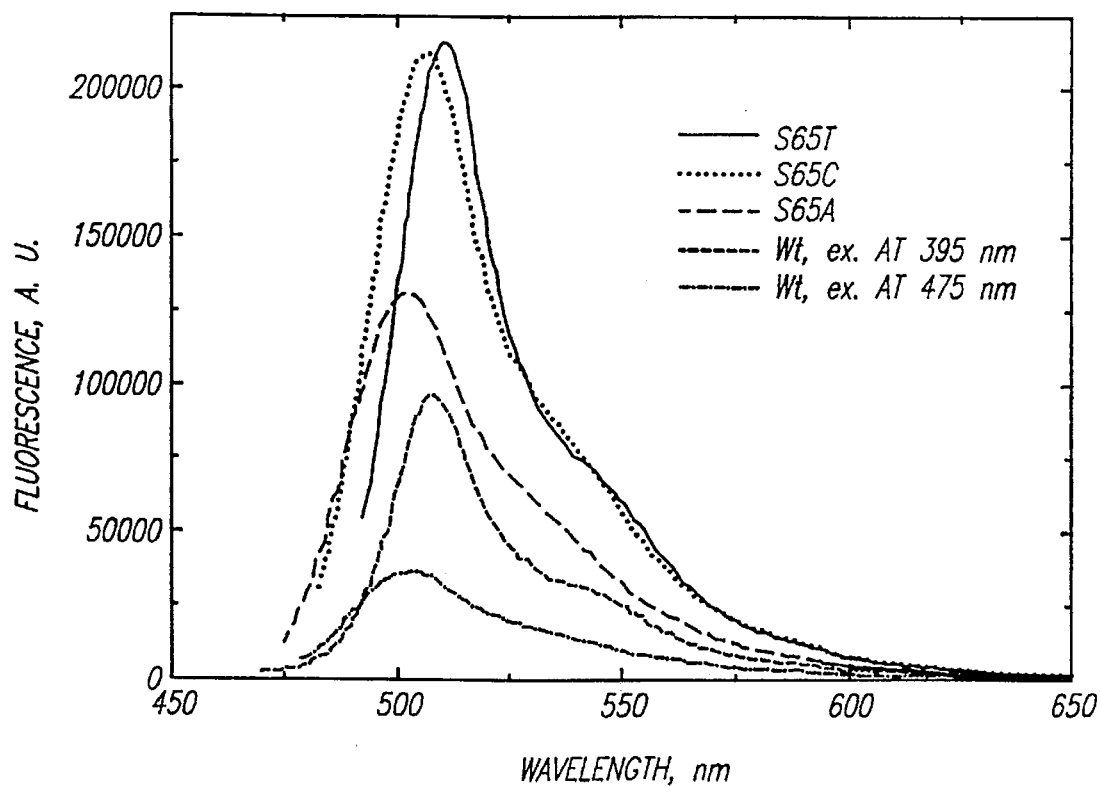

FIGS. 4a and 4b compare the excitation and emission spectra of wild-type and Ser 65 mutants. In FIG. 4a, ——— S65T; — — S65A; - - - S65C; — •— • wild-type (emission at 508 nm). In FIG. 4B, ——— S65T; — — S65A; - - - S65C; • • • wild-type (excitation at 395 nm); — •— • wild-type (excitation at 475 nm). Excitation and emission spectra were measured with 1.8 nm bandwidths and the non-scanning wavelength set to the appropriate peak. As is apparent from FIG. 4b, all three mutants exhibited substantially higher intensity of emission relative to the wild-type protein.

Figure 5:
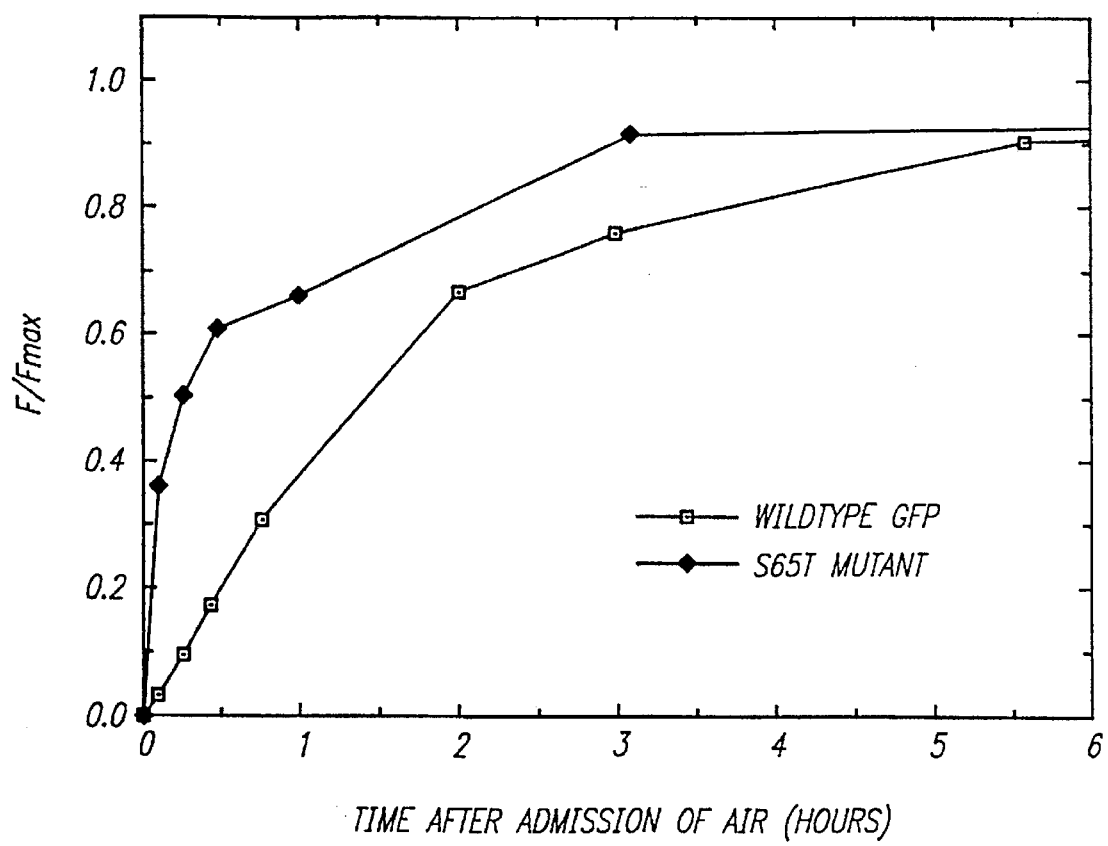
FIG. 5 illustrates the rate of fluorophore formation in the wild-type GFP and the Ser 65→Thr mutant.

FIG. 5 illustrates the rates of fluorophore formation in wild-type GFP and in the Ser 65→Thr mutant. E. coli expressing either wild-type or mutant GFP were grown anaerobically. At time=0, each sample was exposed to air; further growth and protein synthesis were prevented by transferring the cells to nutrient-free medium also containing sodium azide as a metabolic inhibitor. Fluorescence was subsequently monitored as a function of time. For each culture, the fluorescence intensities are expressed as a fraction of the final fluorescence intensity obtained at t=18 to 20 hours, after oxidation had proceeded to completion. From FIG. 5, it is apparent that development of fluorescence proceeds much more quickly in the mutant than in wild-type GFP, even after normalization of the absolute brightnesses (FIGS. 4a and 4b). Therefore, when the development of GFP fluorescence is used as an assay for promotor activation and gene expression, the mutant clearly gives a more rapid and faithful measure than wild-type protein.

Figure 6A:
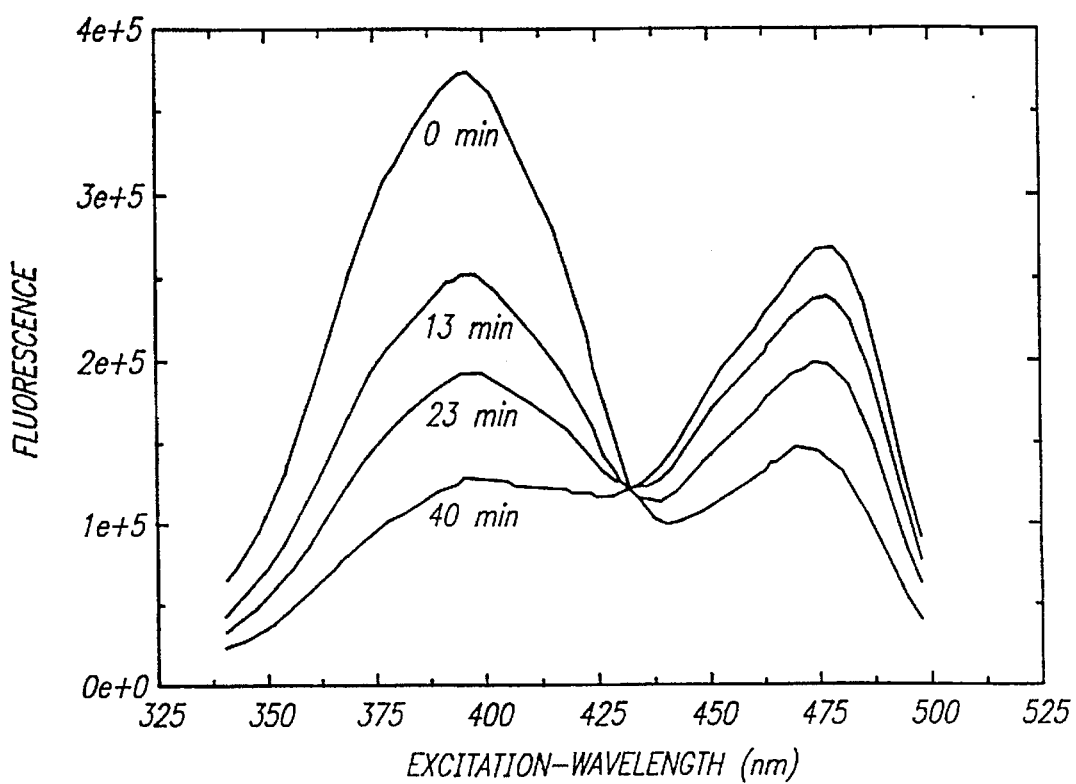
FIGS. 6a and 6b illustrate the behavior of wild-type GFP and the Ser 65→Thr mutant, respectively, upon progressive irradiation with ultraviolet light.
Figure 6B:
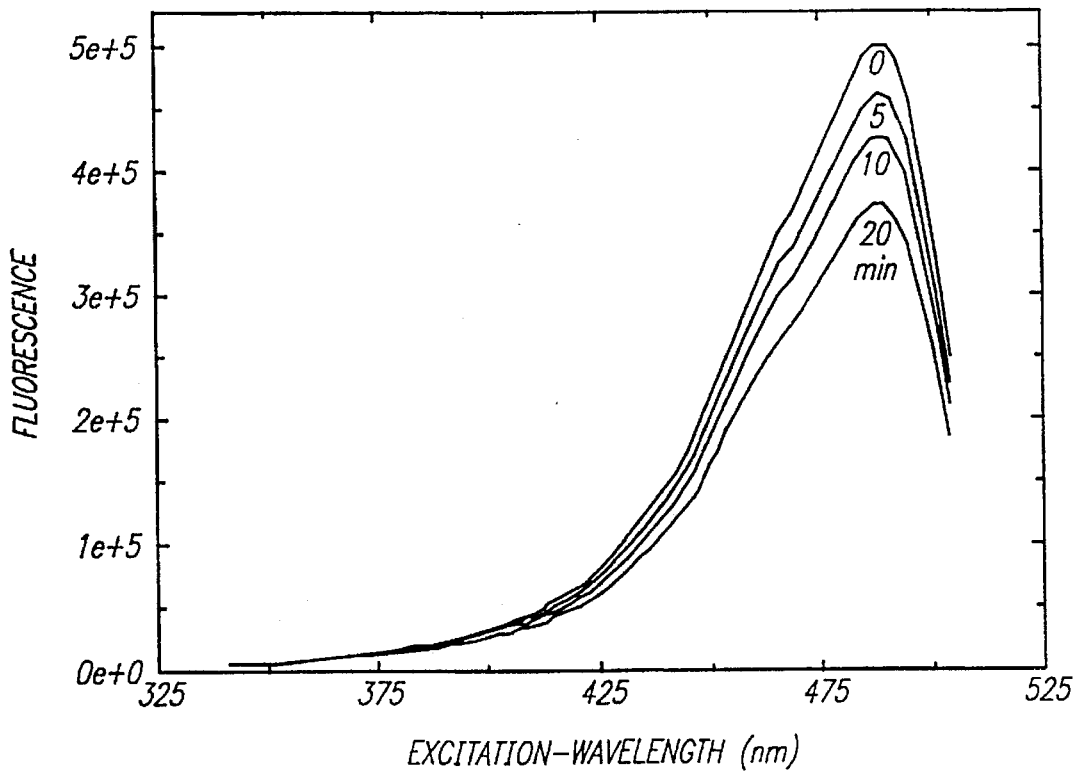

FIGS. 6a and 6b illustrate the behavior of wild-type GFP and the Ser 65→Thr mutant, respectively, upon progressive irradiation with ultraviolet light. Numbers indicate minutes of exposure to illumination at 280 nm; intensity was the same for both samples. Wild-type GFP (FIG. 6a) suffered photoisomerization, as shown by a major change in the shape of the excitation spectrum. Illumination with broad band (240–400 nm) UV caused qualitatively similar behavior but with less increase of amplitude in the 430–500 nm region of the spectrum. The photoisomerization was not reversible upon standing in the dark. This photoisomerization would clearly be undesirable for most uses of wild-type GFP, because the protein rapidly loses brightness when excited at its main peak near 395 nm. The mutant (FIG. 6b) showed no such photoisomerization or spectral shift.

---

What is claimed is:

1. A nucleic acid molecule comprising a nucleotide sequence encoding a functional mutant fluorescent protein whose amino acid sequence differs from the amino acid sequence of Aequorea green fluorescent protein (SEQ ID NO:2) by at least an amino acid substitution selected from the group consisting of T203I, I167V, I167T, Y66H, Y66W, and a substitution at S65, said functional mutant having a different excitation or emission spectrum from Aequorea green fluorescent protein.

2. The nucleic acid molecule of claim 1 encoding a protein comprising the substitution Y66H.

3. The nucleic acid molecule of claim 2 encoding a protein having an excitation maximum at about 382 nm and an emission maximum at about 448 nm.

4. The nucleic acid molecule of claim 1 encoding a protein comprising the substitution T203I.

5. The nucleic acid molecule of claim 4 encoding a protein having an excitation maximum at about 398 nm, no additional excitation maxima near 475 nm, and an emission maximum at about 511 nm.

6. The nucleic acid molecule of claim 1 encoding a protein comprising the substitution Y66W.

7. The nucleic acid molecule of claim 6 encoding a protein having an excitation maximum at about 458 nm and an emission maximum at about 480 nm.

8. The nucleic acid molecule of claim 1 encoding a protein comprising the substitution I167T or I167V.

9. The nucleic acid molecule of claim 8 encoding a protein having an excitation maximum at about 471 nm and an emission maximum at about 502 nm.

10. The nucleic acid molecule of claim 1 encoding a protein comprising a substitution at S65 and having an excitation maximum red-shifted compared to the main peak of Aequorea green fluorescent protein.

11. The nucleic acid molecule of claim 10 encoding a protein comprising the substitution S65A, S65L, S65C, S65V, S65I or S65T.

12. The nucleic acid molecule of claim 11, encoding a protein comprising the substitution S65T.

13. The nucleic acid molecule of claim 1 wherein the nucleotide sequence encodes an amino acid sequence that differs from the amino acid sequence of Aequorea green fluorescent protein (SEQ ID NO:2) by no more than the amino acid substitutions selected from the group consisting of S202F/T203I, I167V, I167T, Y66H, Y66W, and a substitution at S65.

14. The nucleic acid molecule of claim 13 wherein the substitution is S65T.

15. The nucleic acid molecule of any of claims 1–12 encoding a fusion protein wherein the fusion protein comprises a polypeptide of interest and the functional mutant fluorescent protein.

16. The nucleic acid molecule of claim 11 encoding a fusion protein wherein the fusion protein comprises a polypeptide of interest and the functional mutant fluorescent protein wherein the polypeptide of interest comprises a polyhistidine tag.

17. The nucleic acid molecule of claim 1 encoding a fusion protein wherein the fusion protein comprises a polypeptide of interest, the functional mutant fluorescent protein and an oligopeptide spacer between the peptide of interest and the functional mutant fluorescent protein.

18. The nucleic acid molecule of claim 11 encoding a protein comprising the substitution S65C.

19. The nucleic acid molecule of claim 11 encoding a protein comprising the substitution S65V.

20. The nucleic acid molecule of claim 11 encoding a protein comprising the substitution S65I.

21. The nucleic acid molecule of claim 11 encoding a protein comprising the substitution S65A.

22. The nucleic acid molecule of claim 11 encoding a protein comprising the substitution S65L.

23. The nucleic acid of claim 14 encoding a fusion protein wherein the fusion protein comprises a polypeptide of interest and the functional mutant, fluorescent protein.

24. The nucleic acid molecule of claim 14 encoding a fusion protein wherein the fusion protein comprises a polypeptide of interest and the functional mutant fluorescent protein.

25. The nucleic acid molecule of claim 24 wherein the nucleic acid molecule encodes an oligopeptide spacer between the fusion protein and the functional mutant fluorescent protein.

* * * * *

UNITED STATES PATENT AND TRADEMARK OFFICE
CERTIFICATE OF CORRECTION

PATENT NO. : 5,625,048
DATED : 4/29/97
INVENTOR(S) : Tsien et al.

It is certified that error appears in the above-identified patent and that said Letters Patent is hereby corrected as shown below:

Column 12, line 13.
In SEQ ID NO:1, nucleic acid base number 239, replace the "A" with --G--.
In SEQ ID NO:1, amino acid number 80, replace the "Gln" with --Arg--.
In SEQ ID NO:2, amino acid number 80, replace the "Gln" with --Arg--.

Signed and Sealed this

Twenty-seventh Day of July, 1999

Attest:

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 716 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..716

( x i ) SEQUENCE DESCRIPTION: SEQ ID NO:1:

```
ATG  AGT  AAA  GGA  GAA  GAA  CTT  TTC  ACT  GGA  GTT  GTC  CCA  ATT  CTT  GTT         48
Met  Ser  Lys  Gly  Glu  Glu  Leu  Phe  Thr  Gly  Val  Val  Pro  Ile  Leu  Val
 1             5                        10                       15
```

| | | | | | | | | | | | | | | | | |
|---|---|---|---|---|---|---|---|---|---|---|---|---|---|---|---|---|
| GAA | TTA | GAT | GGT | GAT | GTT | AAT | GGG | CAC | AAA | TTT | TCT | GTC | AGT | GGA | GAG | 96 |
| Glu | Leu | Asp | Gly | Asp | Val | Asn | Gly | His | Lys | Phe | Ser | Val | Ser | Gly | Glu | |
| | | | 20 | | | | | 25 | | | | | 30 | | | |
| GGT | GAA | GGT | GAT | GCA | ACA | TAC | GGA | AAA | CTT | ACC | CTT | AAA | TTT | ATT | TGC | 144 |
| Gly | Glu | Gly | Asp | Ala | Thr | Tyr | Gly | Lys | Leu | Thr | Leu | Lys | Phe | Ile | Cys | |
| | | 35 | | | | | 40 | | | | | 45 | | | | |
| ACT | ACT | GGA | AAA | CTA | CCT | GTT | CCA | TGG | CCA | ACA | CTT | GTC | ACT | ACT | TTC | 192 |
| Thr | Thr | Gly | Lys | Leu | Pro | Val | Pro | Trp | Pro | Thr | Leu | Val | Thr | Thr | Phe | |
| | 50 | | | | | 55 | | | | | 60 | | | | | |
| TCT | TAT | GGT | GTT | CAA | TGC | TTT | TCA | AGA | TAC | CCA | GAT | CAT | ATG | AAA | CAG | 240 |
| Ser | Tyr | Gly | Val | Gln | Cys | Phe | Ser | Arg | Tyr | Pro | Asp | His | Met | Lys | Gln | |
| 65 | | | | | 70 | | | | | 75 | | | | | 80 | |
| CAT | GAC | TTT | TTC | AAG | AGT | GCC | ATG | CCC | GAA | GGT | TAT | GTA | CAG | GAA | AGA | 288 |
| His | Asp | Phe | Phe | Lys | Ser | Ala | Met | Pro | Glu | Gly | Tyr | Val | Gln | Glu | Arg | |
| | | | | 85 | | | | | 90 | | | | | 95 | | |
| ACT | ATA | TTT | TTC | AAA | GAT | GAC | GGG | AAC | TAC | AAG | ACA | CGT | GCT | GAA | GTC | 336 |
| Thr | Ile | Phe | Phe | Lys | Asp | Asp | Gly | Asn | Tyr | Lys | Thr | Arg | Ala | Glu | Val | |
| | | | 100 | | | | | 105 | | | | | 110 | | | |
| AAG | TTT | GAA | GGT | GAT | ACC | CTT | GTT | AAT | AGA | ATC | GAG | TTA | AAA | GGT | ATT | 384 |
| Lys | Phe | Glu | Gly | Asp | Thr | Leu | Val | Asn | Arg | Ile | Glu | Leu | Lys | Gly | Ile | |
| | | 115 | | | | | 120 | | | | | 125 | | | | |
| GAT | TTT | AAA | GAA | GAT | GGA | AAC | ATT | CTT | GGA | CAC | AAA | TTG | GAA | TAC | AAC | 432 |
| Asp | Phe | Lys | Glu | Asp | Gly | Asn | Ile | Leu | Gly | His | Lys | Leu | Glu | Tyr | Asn | |
| | 130 | | | | | 135 | | | | | 140 | | | | | |
| TAT | AAC | TCA | CAC | AAT | GTA | TAC | ATC | ATG | GCA | GAC | AAA | CAA | AAG | AAT | GGA | 480 |
| Tyr | Asn | Ser | His | Asn | Val | Tyr | Ile | Met | Ala | Asp | Lys | Gln | Lys | Asn | Gly | |
| 145 | | | | | 150 | | | | | 155 | | | | | 160 | |
| ATC | AAA | GTT | AAC | TTC | AAA | ATT | AGA | CAC | AAC | ATT | GAA | GAT | GGA | AGC | GTT | 528 |
| Ile | Lys | Val | Asn | Phe | Lys | Ile | Arg | His | Asn | Ile | Glu | Asp | Gly | Ser | Val | |
| | | | | 165 | | | | | 170 | | | | | 175 | | |
| CAA | CTA | GCA | GAC | CAT | TAT | CAA | CAA | AAT | ACT | CCA | ATT | GGC | GAT | GGC | CCT | 576 |
| Gln | Leu | Ala | Asp | His | Tyr | Gln | Gln | Asn | Thr | Pro | Ile | Gly | Asp | Gly | Pro | |
| | | | 180 | | | | | 185 | | | | | 190 | | | |
| GTC | CTT | TTA | CCA | GAC | AAC | CAT | TAC | CTG | TCC | ACA | CAA | TCT | GCC | CTT | TCG | 624 |
| Val | Leu | Leu | Pro | Asp | Asn | His | Tyr | Leu | Ser | Thr | Gln | Ser | Ala | Leu | Ser | |
| | | 195 | | | | | 200 | | | | | 205 | | | | |
| AAA | GAT | CCC | AAC | GAA | AAG | AGA | GAC | CAC | ATG | GTC | CTT | CTT | GAG | TTT | GTA | 672 |
| Lys | Asp | Pro | Asn | Glu | Lys | Arg | Asp | His | Met | Val | Leu | Leu | Glu | Phe | Val | |
| | 210 | | | | | 215 | | | | | 220 | | | | | |
| ACA | GCT | GCT | GGG | ATT | ACA | CAT | GGC | ATG | GAT | GAA | CTA | TAC | AAA | TA | | 716 |
| Thr | Ala | Ala | Gly | Ile | Thr | His | Gly | Met | Asp | Glu | Leu | Tyr | Lys | | | |
| 225 | | | | | 230 | | | | | 235 | | | | | | |

(2) INFORMATION FOR SEQ ID NO:2:

(i) SEQUENCE CHARACTERISTICS:
        (A) LENGTH: 238 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | | |
|---|---|---|---|---|---|---|---|---|---|---|---|---|---|---|---|
| Met | Ser | Lys | Gly | Glu | Glu | Leu | Phe | Thr | Gly | Val | Val | Pro | Ile | Leu | Val |
| 1 | | | | 5 | | | | | 10 | | | | | 15 | |
| Glu | Leu | Asp | Gly | Asp | Val | Asn | Gly | His | Lys | Phe | Ser | Val | Ser | Gly | Glu |
| | | | 20 | | | | | 25 | | | | | 30 | | |
| Gly | Glu | Gly | Asp | Ala | Thr | Tyr | Gly | Lys | Leu | Thr | Leu | Lys | Phe | Ile | Cys |
| | | 35 | | | | | 40 | | | | | 45 | | | |
| Thr | Thr | Gly | Lys | Leu | Pro | Val | Pro | Trp | Pro | Thr | Leu | Val | Thr | Thr | Phe |
| | 50 | | | | | 55 | | | | | 60 | | | | |

| | | | | | | | | | | | | | | | |
|---|---|---|---|---|---|---|---|---|---|---|---|---|---|---|---|
| Ser 65 | Tyr | Gly | Val | Gln | Cys 70 | Phe | Ser | Arg | Tyr | Pro 75 | Asp | His | Met | Lys | Gln 80 |
| His | Asp | Phe | Phe | Lys 85 | Ser | Ala | Met | Pro | Glu 90 | Gly | Tyr | Val | Gln | Glu 95 | Arg |
| Thr | Ile | Phe | Phe 100 | Lys | Asp | Asp | Gly | Asn 105 | Tyr | Lys | Thr | Arg | Ala 110 | Glu | Val |
| Lys | Phe | Glu 115 | Gly | Asp | Thr | Leu | Val 120 | Asn | Arg | Ile | Glu | Leu 125 | Lys | Gly | Ile |
| Asp | Phe 130 | Lys | Glu | Asp | Gly | Asn 135 | Ile | Leu | Gly | His | Lys 140 | Leu | Glu | Tyr | Asn |
| Tyr 145 | Asn | Ser | His | Asn | Val 150 | Tyr | Ile | Met | Ala | Asp 155 | Lys | Gln | Lys | Asn | Gly 160 |
| Ile | Lys | Val | Asn | Phe 165 | Lys | Ile | Arg | His | Asn 170 | Ile | Glu | Asp | Gly | Ser 175 | Val |
| Gln | Leu | Ala | Asp 180 | His | Tyr | Gln | Gln | Asn 185 | Thr | Pro | Ile | Gly | Asp 190 | Gly | Pro |
| Val | Leu | Leu 195 | Pro | Asp | Asn | His | Tyr 200 | Leu | Ser | Thr | Gln | Ser 205 | Ala | Leu | Ser |
| Lys | Asp 210 | Pro | Asn | Glu | Lys | Arg 215 | Asp | His | Met | Val | Leu 220 | Leu | Glu | Phe | Val |
| Thr 225 | Ala | Ala | Gly | Ile | Thr 230 | His | Gly | Met | Asp | Glu 235 | Leu | Tyr | Lys | | |